United States Patent
Pillai et al.

(10) Patent No.: US 9,585,388 B2
(45) Date of Patent: Mar. 7, 2017

(54) SYNERGISTICALLY ACTING TERNARY ANTIMICROBIAL MIXTURES

(71) Applicant: SYMRISE AG, Holzminden (DE)

(72) Inventors: Ravikumar Pillai, Emerson, NJ (US);
Antje Köhler, Holzminden (DE);
Gerhard Schmaus, Höxter-Bosseborn (DE)

(73) Assignee: Symrise AG, Holzminden (DE)

( * ) Notice: Subject to any disclaimer, the term of this patent is extended or adjusted under 35 U.S.C. 154(b) by 562 days.

(21) Appl. No.: 13/668,560

(22) Filed: Nov. 5, 2012

(65) Prior Publication Data

US 2013/0136709 A1 May 30, 2013

(30) Foreign Application Priority Data

Nov. 4, 2011 (DE) .................. 10 2011 085 798

(51) Int. Cl.
| | | |
|---|---|---|
| *A61Q 15/00* | (2006.01) | |
| *A61K 8/34* | (2006.01) | |
| *A01N 31/14* | (2006.01) | |
| *A01N 31/02* | (2006.01) | |
| *A61K 31/047* | (2006.01) | |
| *A61K 31/085* | (2006.01) | |
| *A61Q 17/00* | (2006.01) | |
| *A61K 9/00* | (2006.01) | |
| *A23L 3/3481* | (2006.01) | |
| *A61Q 1/02* | (2006.01) | |
| *A61Q 5/02* | (2006.01) | |
| *A61Q 17/04* | (2006.01) | |
| *A61Q 19/00* | (2006.01) | |

(52) U.S. Cl.
CPC .............. *A01N 31/14* (2013.01); *A01N 31/02* (2013.01); *A23L 3/3481* (2013.01); *A61K 8/34* (2013.01); *A61K 8/345* (2013.01); *A61K 9/0014* (2013.01); *A61K 31/047* (2013.01); *A61K 31/085* (2013.01); *A61Q 15/00* (2013.01); *A61Q 17/005* (2013.01); *A61K 2800/524* (2013.01); *A61K 2800/5922* (2013.01); *A61Q 1/02* (2013.01); *A61Q 5/02* (2013.01); *A61Q 17/04* (2013.01); *A61Q 19/00* (2013.01)

(58) Field of Classification Search
None
See application file for complete search history.

(56) References Cited

U.S. PATENT DOCUMENTS

| | | | | |
|---|---|---|---|---|
| 7,582,681 B2 * | 9/2009 | Schmaus et al. | ............. | 514/738 |
| 2007/0265352 A1 * | 11/2007 | Roeding et al. | ............. | 514/738 |

FOREIGN PATENT DOCUMENTS

| | | |
|---|---|---|
| DE | 20221386 U1 | 10/2005 |
| WO | WO-03069994 A1 | 8/2003 |
| WO | WO-2005102276 A1 | 11/2005 |
| WO | WO2008119841 A2 * | 10/2008 |

OTHER PUBLICATIONS

JP 11-322591 English Translation.*
JP 11-322591 English Translation (1999).*
Extended European Search Report, European Patent Application No. 12188081.9, dated Mar. 8, 2013.
Official Communication, European Application No. EP20120188081.
Third Party Observation, European Application No. EP20120188081.

* cited by examiner

*Primary Examiner* — Robert A Wax
*Assistant Examiner* — Randeep Singh
(74) *Attorney, Agent, or Firm* — Dilworth & Barrese, LLP

(57) ABSTRACT

The invention relates to synergistically effective ternary antimicrobial mixtures.

4 Claims, No Drawings

SYNERGISTICALLY ACTING TERNARY ANTIMICROBIAL MIXTURES

CROSS-REFERENCE TO RELATED APPLICATION

This application claims priority under 35 U.S.C. §119(a) to German Application No. 10 2011 085 798.2, filed Nov. 4, 2011, the entire contents of which is hereby incorporated by reference.

STATEMENT REGARDING FEDERALLY SPONSORED RESEARCH OF DEVELOPMENT

Not Applicable

THE NAMES OF THE PARTIES TO A JOINT RESEARCH AGREEMENT

Not Applicable

INCORPORATION-BY-REFERENCE OF MATERIAL SUBMITTED ON A COMPACT DISC

Not Applicable

BACKGROUND OF THE INVENTION

Field of the Invention

The present invention relates to the area of antimicrobial active substances and in particular certain mixtures, preparations and foodstuffs comprising 2-phenoxyethanol, and at least two different alkanediols, selected from the group consisting of 1,2-decanediol, 1,2-octanediol, 1,2-hexanediol and 1,2-pentanediol. The invention further relates to the use of 2-phenoxyethanol for synergistic intensification of the antimicrobial efficacy of mixtures of at least two of the aforementioned alkanediols, a method of preservation or antimicrobial treatment of a perishable product, a method of cosmetic treatment of certain microorganisms and the use of a mixture according to the invention for the therapeutic treatment of certain microorganisms.

Description of Related Art

In the cosmetics, pharmaceutical and food industry there is a constant demand for agents with antimicrobial properties, in particular for the preservation of otherwise perishable products (e.g. cosmetics, pharmaceutical products or foodstuffs), but also for the direct cosmetic or therapeutic treatment of microorganisms, which may have an adverse influence on the human body or animal body. As an example, reference may be made to microorganisms that can cause body odour, acne, mycoses or the like.

A large number of antimicrobial active substances are admittedly already used in the aforementioned technical areas, but further alternatives are still sought, in order to be able to carry out targeted special treatments and/or to reduce side-effects. When searching for alternative agents with antimicrobial and in particular preservative action, it must however be borne in mind that the substances used in the cosmetic, pharmaceutical and/or foodstuff area must be
    toxicologically harmless,
    well-tolerated by the skin,
    stable (in particular in the usual cosmetic and/or pharmaceutical formulations),
    largely and preferably completely odourless and/or
    producible at low cost (i.e. using standard processes and/or starting from standard precursors).

Moreover, it is desirable to have to use as little as possible of the antimicrobial active substances in the corresponding agents, to achieve a certain antimicrobial effect.

The search for suitable (active) substances that possess one or more of the aforementioned properties to a sufficient degree is made difficult for a person skilled in the art because there is no clear relationship between the chemical structure of a substance on the one hand and its biological activity against certain microorganisms (microbes) and its stability, on the other hand. Furthermore, there is no predictable relationship between antimicrobial action, toxicological harmlessness, skin compatibility and the stability of a substance.

BRIEF SUMMARY OF THE INVENTION

The object to be solved by the present invention was therefore to provide agents that meet several or all of the aforementioned requirements and/or possess a desirable combination of the aforementioned properties.

This object is solved by a mixture comprising or consisting of
(a) 2-phenoxyethanol and
(b1+b2) at least two different alkanediols, selected from the group consisting of 1,2-decanediol, 1,2-octanediol, 1,2-hexanediol and 1,2-pentanediol.

The invention is based on the surprising finding that the ternary mixtures according to the invention can display a synergistically intensified antimicrobial effect at least against selected microbes, in particular against *Aspergillus niger*, a mould that is very difficult to control.

In particular it has been found that the mixtures according to the invention are excellent for use as an antimicrobial mixture, in particular for preserving otherwise perishable goods (see above).

BRIEF DESCRIPTION OF THE SEVERAL VIEWS OF THE DRAWINGS

Not Applicable

DETAILED DESCRIPTION OF THE INVENTION

Although specialists have already conducted extensive investigations of the antimicrobial properties of 1,2-alkanediols and 2-phenoxyethanol, there had previously been no indication that the ternary mixtures of such compounds according to the invention possess, at least in an isolated case, a definitely improved antimicrobial action (at least against selected microbes).

The antimicrobial action of 2-phenoxyethanol, a widely used preservative, is known and is described for example in the "Handbuch der Konservierungsmittel" [Preservatives Handbook] (Publ.: Deutsche Gesellschaft für wissenschaftliche und angewandte Kosmetik, Verlag für chemische Industrie, H. Ziolkowsky GmbH, D-86150 Augsburg, 1995). To date, however, research into a synergistically intensified efficacy of a ternary combination with 1,2-decanediol and 1,2-hexanediol in particular against *Aspergillus niger* has not been disclosed in any document.

The antimicrobial action of polyols, especially of aliphatic 1,2-diols and combinations of 1,2-diols with other substances with antimicrobial action is described in various documents. We may mention for example JP5191327, JP11322591, EP1206933, WO 03/069994. However, research into a synergistically intensified efficacy against *Aspergillus niger* in combination with 2-phenoxyethanol is not disclosed in any of these documents.

Polyols and in particular 1,2-alkanediols are mostly inadequately effective against moulds such as *Aspergillus niger*. With respect to individual polyols or mixtures of polyols, there is thus a gap in efficacy in the case of moulds (e.g. the "problem germ" *Aspergillus niger*). Therefore complete inhibition of moulds has until now required the use of high concentrations of individual polyols or of mixtures of polyols.

It was therefore particularly surprising that the mixtures according to the invention display a strongly synergistic efficacy. For example in the treatment of *Aspergillus niger* individually dosed 2-phenoxyethanol
  individually dosed 1,2-decanediol
  individually dosed 1,2-hexanediol
  individually dosed 1,2-octanediol
  individually dosed 1,2-pentanediol as well as mixtures containing two or more of these diols are already far superior after 48 hours with respect to reduction in microbial count, when they are contained at the same usage concentration in the end products that are to be protected against microbial attack. In particular, at given concentrations, only said ternary mixtures according to the invention already achieved an almost 2-log reduction in microbial count after 48 h.

Owing to the particularly significant intensification of the action of their constituents, mixtures according to the invention are suitable in particular for combating *Aspergillus niger* even at low dosage of the mixture according to the invention.

Preferred according to the invention in this sense is a mixture according to the invention comprising or consisting of
(a) 2-phenoxyethanol,
(b1) 1,2-decanediol
and
(b2) 1,2-hexanediol and/or 1,2-pentanediol.

A mixture according to the invention in which the weight ratio of component (a) to component (b1+b2) is 0.3-1.2 to 0.06-0.7, and in particular in which the weight ratios of the components (a) to (b1) to (b2) are 0.3-1.2 to 0.05-0.4 to 0.01-0.3, is particularly preferred.

A mixture according to the invention in which the weight ratios of the components (a) to (b1+b2) and/or (a) to (b1) to (b2) are adjusted in such a way that the antimicrobial action is synergistically intensified, is particularly preferred.

Through suitable selection of the concentrations of the components (a), (b1) and (b2) and selection of the mixture ratios of the components to one another, a synergistic effect can therefore be achieved with respect to the antimicrobial action. As already mentioned above, this was surprising. The synergistic effect has the advantage that for the same efficacy, less antimicrobially active substance has to be used, or with the same amount of active substance, an improved antimicrobial effect can be achieved.

In case of doubt, antimicrobial efficacy in the sense of this text is present when adequate preservation is established according to the European Pharmacopoeia (ISBN 3-7692-2768-9; Supplement 2001 to the 3rd Edition, page 421-422, chapter 5.1.3). The microbe preferably to be used is preferably *Aspergillus niger* ATCC16404. For further information on the procedure for testing for antimicrobial efficacy, reference is made in particular to example 1 given below.

Synergistic intensification (of antimicrobial action) is present when the synergy index (SI value) of the test mixture according to Kull (literature: F. C. Kull et al., Applied Microbiology Vol. 9, p. 538-541 (1961); D. C. Steinberg, Cosmetics & Toiletries Vol. 115(11), 59-62 (2000)) gives a value <1. For further information on calculation of the synergy index, reference is again made to example 1 given below. Once again, the microbe preferably to be used for determining the synergy index is the strain of *Aspergillus niger* stated above.

A particularly preferred mixture according to the invention is one in which component (b1) consists of 1,2-decanediol and component (b2) consists of 1,2-hexanediol. A particularly large synergistic effect with respect to antimicrobial efficacy can be achieved in the resultant ternary system prepared from 2-phenoxyethanol, 1,2-decanediol and 1,2-hexanediol.

The antimicrobial mixtures according to the invention are suitable for the preservation and antimicrobial treatment of perishable products, e.g. cosmetics, pharmaceutical products or foodstuffs. The perishable product is contacted with an amount of a mixture according to the invention that is antimicrobially effective, preferably effective against *Aspergillus niger*. However, owing to their synergistically intensified antimicrobial efficacy, the mixtures according to the invention can also be used
  (a) for cosmetic (in particular also topical) treatment of microorganisms that cause body odour,
  (b) for cosmetic (in particular also topical) treatment of microorganisms that cause acne,
  (c) for cosmetic (in particular also topical) treatment of microorganisms that cause mycoses and
  (d) for the treatment of microorganisms on or in inanimate matter.

The mixtures according to the invention develop their synergistically intensified antimicrobial action against a large number of Gram-positive bacteria, Gram-negative bacteria, moulds and yeasts. There is particularly good action against Gram-negative bacteria such as *Escherichia coli* and *Pseudomonas aeruginosa*, against yeasts such as *Candida albicans* and—as mentioned above—also against fungi such as *Aspergillus niger*. The very good efficacy of the mixtures according to the invention against *Aspergillus niger*, a mould that is very difficult to control, is to be regarded as particularly advantageous.

The invention also relates to the use of a mixture according to the invention for the therapeutic treatment of
(i) microorganisms that cause body odour,
(ii) microorganisms that cause acne and/or
(iii) microorganisms that cause mycoses,
or as agents for the therapeutic treatment of
(i) microorganisms that cause body odour,
(ii) microorganisms that cause acne and/or
(iii) microorganisms that cause mycoses.

The present invention therefore relates to corresponding methods for cosmetic and/or therapeutic treatment of microbes, and indeed in particular of (a) microorganisms that cause body odour, (b) microorganisms that cause acne and/or (c) microorganisms that cause mycoses, comprising the topical application of an antimicrobially effective amount of a mixture according to the invention, wherein preferably the proportions of said diols in the mixture preferably are adjusted in such a way that their antimicrobial action is synergistically intensified.

Preferred forms of the methods according to the invention correspond to the preferred forms of the use according to the invention described above.

The human skin is colonised by a large number of various microorganisms, including the microorganisms already mentioned above, plus others. The majority of these microorganisms are not pathogenic and have no relevance for the physiological state of the skin and for its odour. Others, however, can have a decisive influence on the healthy state of the skin.

As our own investigations have shown, the synergistically active mixtures according to the invention are very effective not only against the microbes already mentioned above, but also against *Staphylococcus epidermidis, Corynebacterium xerosis, Brevibacterium epidermidis, Propionibacterium acnes* and against *Trichophyton* and *Epidermophyton* species, so that they can also be used as agents for treating (controlling) underarm and foot odour or body odour in general, as agents for combating acne, as antidandruff agents and for treating mycoses (in particular dermatomycoses).

"Treatment" means, in the context of the present text, any form of therapeutic or non-therapeutic exertion of influence on the relevant microorganisms, in which the multiplication of said microorganisms is inhibited and/or the microorganisms are killed.

The invention relates to a cosmetic or pharmaceutical preparation or a foodstuff, comprising
  an antimicrobially effective mixture according to any one of the preceding claims and
  further usual constituents.

A cosmetic or pharmaceutical preparation according to the invention or a foodstuff according to the invention, wherein the total amount of the components (a) and (b1+b2) and/or the total amount of the components (a), (b1) and (b2) is in the range from 0.01 to 10 wt %, relative to the total mass of the preparation or of the foodstuff, is preferred.

A cosmetic or pharmaceutical preparation according to the invention or a foodstuff according to the invention is thereby particularly preferred, comprising
  0.30 to 1.20 wt % of 2-phenoxyethanol
  0.05 to 0.40 wt % of 1,2-decanediol
  and
0.01 to 0.30 wt % of the total amount of 1,2-hexanediol and/or 1,2-pentanediol,
in each case relative to the total mass of the preparation or of the foodstuff, is particularly preferred.

Furthermore, a cosmetic or pharmaceutical preparation according to the invention or a foodstuff according to the invention is further preferred that comprises 2-phenoxyethanol as component (a), 1,2-decanediol as component (b1) and 1,2-hexanediol and/or 1,2-pentanediol as component (b2), with a proportion of (a) 70 wt % of 2-phenoxyethanol, (b1) 0.20 wt % of 1,2-decanediol and 0.1 wt % of the total amount of 1,2-hexanediol and/or 1,2-pentanediol, relative to the total mass of the preparation or of the foodstuff.

For the preparations according to the invention or foodstuffs according to the invention that have just been described, with increasing preference the particular antimicrobial effects, and in particular the synergistic intensification of these effects, is in each case further improved.

Accordingly, furthermore, a cosmetic or pharmaceutical preparation according to the invention or a foodstuff according to the invention is quite particularly preferred, wherein the concentration of each of the components (a), (b1) and (b2) in itself is below the antimicrobially effective concentration, but the total concentration of the components (a), (b1) and (b2) is antimicrobially effective. In this connection it is particularly preferable that the proportions of the component (a) are in the range from 0.5 to 1 wt %, those of the component (b1) are in the range from 0.1 to 0.3 wt % and those of the component (b2) are in the range from 0.05 to 0.2 wt %.

Also in a preferred method according to the invention for cosmetic and/or therapeutic treatment of (a) microorganisms that cause body odour, (b) microorganisms that cause acne and/or (c) microorganisms that cause mycoses, the concentration to be used of the synergistically active mixtures according to the invention is in the range between 0.01 and 10 wt % and particularly preferably in the range between 0.05 and 5 wt %, in each case relative to the total mass of the cosmetic or pharmaceutical product that the mixture comprises.

The synergistically active mixtures can be used (a) prophylactically or (b) when required.

The concentration of the amount of active substance e.g. to be applied daily varies and depends on the physiological state of the subject and parameters specific to the individual such as age or body weight. The synergistically active mixtures according to the invention can be used both alone and in combination with other substances with antimicrobial action.

It should be pointed out that the 1,2-alkanediols to be used according to the invention in the context of the present text can both be in the form of the corresponding 2S-configured enantiomer and as the 2R-configured enantiomer and in the form of any mixtures of these 2S- and 2R-configured enantiomers. For commercial reasons, it is indeed particularly advantageous to use mixtures of racemates of the respective 1,2-alkanediols to be used according to the invention for controlling microorganisms, as these are particularly easily accessible synthetically, but the pure enantiomers or non-racemic mixtures of these enantiomers are also suitable for the purposes according to the invention.

Further uses/methods and mixtures/compositions according to the invention can be seen from the following account and the appended patent claims.

Preparations that contain a mixture according to the invention are, especially if they are used against microbes that cause body odour, as a rule applied topically in the form of solutions, creams, lotions, gels, sprays or the like. For other purposes, oral (tablets, capsules, powder, drops), intravenous, intraocular, intraperitoneal or intramuscular application or application in the form of an impregnated dressing is appropriate in some cases.

The mixtures according to the invention can be incorporated without difficulty in common cosmetic or dermatological formulations (preparations) such as, among others, pump sprays, aerosol sprays, creams, ointments, tinctures, lotions, nail care products (e.g. nail varnishes, nail varnish remover, nail balsams) and the like. It is also possible, and in some cases advantageous, to combine the (synergistic) mixtures according to the invention with further active substances, for example with other substances with antimicrobial, antimycotic or antiviral action. The cosmetic and/or dermatological/keratological formulations containing the (synergistic) mixtures according to the invention can otherwise be formulated as usual and be used for treatment of the skin and/or of the hair in the sense of a dermatological treatment or a treatment in the sense of care cosmetics. However, they can also be used in make-up products in decorative cosmetics.

If the mixtures according to the invention are used as active substances for the preservation of organic material, then additionally a further or several further preservatives can be used advantageously. It is preferable to select preservatives such as benzoic acid, the esters and salts thereof, propionic acid and salts thereof, salicylic acid and salts thereof, 2,4-hexadienoic acid (sorbic acid) and salts thereof, formaldehyde and paraformaldehyde, 2-hydroxybiphenyl ether and salts thereof, 2-zinc sulphidopyridine-N-oxide, inorganic sulphites and bisulphites, sodium iodate, chlorobutanol, 4-ethyl mercury(II)-5-amino-1,3-bis(2-hydroxybenzoic acid), salts and esters thereof, dehydroacetic acid, formic acid, 1,6-bis(4-amidino-2-bromophenoxy)-n-hexane and salts thereof, the sodium salt of ethyl mercury(II)-thiosalicylic acid, phenyl mercury and salts thereof, 10-undecylenic acid and salts thereof, 5-amino-1,3-bis(2-ethylhexyl)-5-methyl-hexahydropyrimidine, 5-bromo-5-nitro-1,3-dioxane, 2-bromo-2-nitro-1,3-propanediol, 2,4-dichlorobenzyl alcohol, N-(4-chlorophenyl)-N'-(3,4-dichlorophenyl)-urea, 4-chloro-m-cresol, 2,4,4'-trichloro-2'-hydroxydiphenyl ether, 4-chloro-3,5-dimethylphenol, 1,1'-methylene-bis(3-(1-hydroxymethyl-2,4-dioximidazolidin-5-yl)urea), poly-(hexamethylenediguanide) hydrochloride, 2-phenoxyethanol, hexamethylenetetramine, 1-(3-chloroallyl)-3,5,7-triaza-1-azonia-adamantane chloride, 1(4-chlorophenoxy)1(1H-imidazol-1-yl)-3,3-dimethyl-2-butanone, 1,3-bis(hydroxymethyl)-5,5-dimethyl-2.4-imidazolidinedione, benzyl alcohol, octopirox, 1,2-dibromo-2,4-dicyanobutane, 2,2'-methylene-bis(6-bromo-4-chlorophenol), bromochlorophen, mixture of 5-chloro-2-methyl-3(2H)-isothiazolinone and 2-methyl-3(2H)isothiazolinone with magnesium chloride and magnesium nitrate, 2-benzyl-4-chlorophenol, 2-chloroacetamide, chlorhexidine, chlorhexidine acetate, chlorhexidine gluconate, chlorhexidine hydrochloride, 1-phenoxy-propan-2-ol, N-alkyl($C_{12}$-$C_{22}$)trimethylammonium bromide and chloride, 4,4-dimethyl-1,3-oxazolidine, N-hydroxymethyl-N-(1,3-di(hydroxymethyl)-2,5-dioxoimidazolidin-4-yl)-N'-hydroxymethylurea, 1,6-bis(4-amidino-phenoxy)-n-hexane and salts thereof, glutaraldehyde, 5-ethyl-1-aza-3,7-dioxabicyclo(3.3.0)octane, 3-(4-chlorophenoxy)-1,2-propanediol, hyamines, alkyl-($C_8$-$C_{18}$)-dimethylbenzylammonium chloride, alkyl-($C_8$-$C_{18}$)-dimethylbenzylammonium bromide, alkyl-($C_8$-$C_{18}$)-dimethylbenzylammonium saccharinate, benzylhemiformal, 3-iodo-2-propinyl-butylcarbamate, sodium hydroxymethyl-aminoacetate or sodium hydroxymethyl-aminoacetate [sic].

If the mixtures according to the invention are used primarily for inhibiting the growth of undesirable microorganisms on or in animal organisms, combination with further substances with antibacterial or antimycotic action is also advantageous in some cases. To that extent, as further active substances, in addition to the large group of classical antibiotics, mention may be made in particular of the cosmetics-relevant products such as triclosan, climbazole, octoxyglycerol, octopirox (1-hydroxy-4-methyl-6-(2,4,4-trimethylpentyl)-2(1H)-pyridone, 2-aminoethanol), chitosan, farnesol, glycerol monolaurate, aliphatic and aromatic hydroxamic acids, tropolon, hinokitiol or combinations of the aforementioned substances, which among other things are used against underarm odour, foot odour or dandruff.

The mixtures according to the invention can, especially in cosmetic preparations, advantageously be combined with further usual constituents, for example:

Other preservatives, other antimicrobial agents, for example other antibacterial agents or fungicides, abrasives, anti-acne agents, agents against skin ageing, anticellulitis agents, antidandruff agents, anti-inflammatory agents, irritation-preventing agents, irritation-inhibiting agents, anti-oxidants, astringents, sweat-inhibiting agents, antiseptic agents, antistatic agents, binders, buffers, carrier materials, chelating agents, cell stimulants, cleansing agents, care agents, depilatory agents, surface active substances, deodorizing agents, antiperspirants, plasticisers, emulsifiers, enzymes, essential oils, fibres, film forming agents, fixatives, foam formers, foam stabilisers, antifoaming substances, foam boosters, gelling agents, gel-forming agents, hair care agents, hair shaping agents, hair smoothing agents, hydrating agents, moisturisers, humectants, bleaching agents, strengthening agents, stain removing agents, optical brighteners, impregnating agents, dirt repellents, friction-reducing agents, lubricants, moisturizing creams, ointments, opacifiers, plasticising agents, opacifying agents, polishes, lustre agents, polymers, powders, proteins, refatting agents, abrading agents, silicones, skin calming agents, skin cleaning agents, skin care agents, skin healing agents, skin lightening agents, skin-protecting agents, skin softening agents, cooling agents, skin cooling agents, warming agents, skin-warming agents, stabilisers, UV-absorbents, UV-filters, detergents, fabric softeners, suspending agents, skin-tanning agents, thickeners, vitamins, oils, waxes, fats, phospholipids, saturated fatty acids, singly or multiply unsaturated fatty acids, α-hydroxy acids, polyhydroxy fatty acids, liquefiers, dyes, colour-protecting agents, pigments, anticorrosive agents, aromas, flavouring materials, odoriferous substances, polyols, surfactants, electrolytes, organic solvents or silicone derivatives.

Furthermore, the mixtures according to the invention can also be used in combination with sweat-inhibiting active substances (antiperspirants) particularly advantageously for combating body odour. Aluminium salts such as aluminium chloride, aluminium hydrochloride, nitrate, sulphate, acetate etc. are mainly used as antiperspirants. In addition, however, the use of zinc, magnesium and zirconium compounds may also be advantageous. Essentially the aluminium salts and—to a somewhat lesser extent—aluminium/zirconium salt combinations have proved suitable for use in cosmetic and dermatological antiperspirants. In addition, the aluminium hydroxychlorides that are partially neutralised and therefore better tolerated by the skin, but are not quite so effective, may also be mentioned.

If the mixtures according to the invention are used for antimicrobial treatment of a surface (e.g. of a human or animal body), in some cases a combination with (metal) chelating agents is advantageous. Preferred (metal) chelating agents to be used are, among others, α-hydroxy fatty acids, phytic acid, lactoferrin, α-hydroxy acids such as, among others, citric acid, lactic acid and malic acid and humic acids, bile acids, bile extracts, bilirubin, biliverdin or EDTA, EGTA and derivatives thereof.

For use, the mixtures according to the invention with cosmetic and/or dermatological action are applied in sufficient amount on the skin and/or on the hair in the manner that is usual for cosmetics and skin remedies. Particular advantages are offered by cosmetic and dermatological preparations that contain a mixture according to the invention and additionally act as sunscreen agents. Advantageously these preparations contain at least one UVA filter and/or at least one UVB filter and/or at least one inorganic pigment. The preparations can be in various forms, for example such as are usually employed for sunscreen preparations. For example, they can be in the form of a solution, an emulsion of the water-in-oil (W/O) type or of the oil-in-water (O/W) type, or a multiple emulsion, for example of the water-in-oil-in-water (W/O/W) type, a gel, an aqueous dispersion, a solid stick or also an aerosol.

As already mentioned, preparations that contain a mixture according to the invention can advantageously be combined with substances that absorb UV radiation, wherein the total amount of the filter substances is e.g. 0.01 wt % to 40 wt %, preferably 0.1% to 10 wt %, in particular 1.0 to 5.0 wt %, relative to the total weight of the preparations, in order to provide cosmetic preparations that protect the hair or the skin against ultraviolet radiation.

In formulations containing mixtures according to the invention for topical prophylactic or cosmetic treatment of the skin, a high proportion of care substances is regularly advantageous. According to a preferred embodiment, the compositions contain one or more animal and/or plant fats and oils such as olive oil, sunflower oil, refined soya oil, palm oil, sesame oil, rape oil, almond oil, borage oil, evening primrose oil, coconut oil, shea butter, jojoba oil, sperm oil, beef tallow, neatsfoot oil and lard for maintenance care and optionally other constituents for maintenance care, for example fatty alcohols with 8-30 carbon atoms.

Care substances that can be combined excellently with the synergistic mixtures according to the invention also include
  ceramides, wherein ceramides are to be understood as
    N-acylsphingosines (fatty acid amides of sphingosine) or synthetic analogues of such lipids (so-called pseudoceramides), which greatly improve the water-retaining capacity of the stratum corneum.
  phospholipids, for example soya lecithin, egg lecithin and kephalins
  petroleum jelly, paraffin oils and silicone oils; the latter include, among others, dialkyl and alkaryl siloxanes such as dimethylpolysiloxane and methylphenylpolysiloxane, and alkoxylated and quaternised derivatives thereof.

Cosmetic preparations that contain mixtures according to the invention can also contain antioxidants, wherein all antioxidants that are suitable or usual for cosmetic and/or dermatological applications can be used.

Cosmetic preparations that contain mixtures according to the invention can also contain vitamins and vitamin precursors, wherein all vitamins and vitamin precursors that are suitable or usual for cosmetic and/or dermatological applications can be used. We may mention in particular vitamins and vitamin precursors such as tocopherols, vitamin A, nicotinic acid and nicotinamide, other B-complex vitamins, in particular biotin and vitamin C, panthenol and derivatives thereof, in particular the esters and ethers of panthenol and cationically derivatised panthenols, for example panthenol triacetate, panthenol monoethyl ether and its monoacetate and cationic panthenol derivatives.

Cosmetic preparations that contain mixtures according to the invention can also contain anti-inflammatory agents or active substances for alleviating reddening or pruritus. All anti-inflammatory agents or active substances alleviating reddening and pruritus that are suitable or usual for cosmetic and/or dermatological applications can be used.

Cosmetic preparations that contain mixtures according to the invention can also contain active substances with skin-lightening or skin-tanning action. According to the invention, all skin-lightening or skin-tanning active substances that are suitable or usual for cosmetic and/or dermatological applications can be used.

Cosmetic preparations that contain mixtures according to the invention can also contain anionic, cationic, non-ionic and/or amphoteric surfactants, especially when crystalline or microcrystalline solids, for example inorganic micropigments, are to be incorporated in the preparations.

The invention is explained in more detail below, on the basis of examples. Unless stated otherwise, data refer to weight.

Example 1

Synergistic Efficacy of the Ternary Mixtures According to the Invention

A comparison was carried out for adequate preservation of cosmetic formulations containing 2-phenoxyethanol (product A, not according to the invention), 1,2-decanediol (product B, not according to the invention), 1,2-hexanediol (product C, not according to the invention), a binary mixture of 2-phenoxyethanol and 1,2-hexanediol (product D, not according to the invention), a binary mixture of 2-phenoxyethanol and 1,2-decanediol (product E, not according to the invention), a binary mixture of 1,2-decanediol and 1,2-hexanediol (product F, not according to the invention) and a ternary mixture of 2-phenoxyethanol, 1,2-decanediol and 1,2-hexanediol (product G, according to the invention).

The test for adequate preservation was carried out according to the European Pharmacopoeia.

Thus, the test consists of contaminating the preparation, if possible in its final proportions, with a specified inoculum of suitable microorganisms, storing the inoculated preparation at a specified temperature, removing the samples from the container at specified time intervals and determining the number of microorganisms in the samples removed. The preserving properties are adequate if, in the test conditions, there is a clear decrease or optionally no increase of the microbial count in the inoculated preparations after the specified times at the specified temperatures. Experimental details of the test procedure are described in the European Pharmacopoeia (ISBN 3-7692-2768-9; Supplement 2001 to the 3rd Edition, p. 421-422, chapter 5.1.3).

Test Organisms:
The following strains of microorganisms were used for the tests for adequate preservation:
A: *Escherichia coli* ATCC 8739
B: *Pseudomonas aeruginosa* ATCC 9027
C: *Staphylococcus aureus* ATCC 6538
D: *Candida albicans* ATCC 10231
E: *Aspergillus niger* ATCC 16404

The initial microbial count (CFU/g; Colony Forming Units/g; "0" value) was in the range from 1 000 000 to 1 200 000 in the various test series.

Formulation:
For the tests for adequate preservation, the combination of active substances according to the invention (product G) was incorporated in a defined amount in an O/W emulsion. For comparison, the comparative products (product A to F) were incorporated in separate O/W emulsions.

TABLE 1

Formulations with products A to G

|  | INCI name | Manufacturer | wt % with "A" | wt % with "B" | wt % with "C" | wt % with "D" | wt % with "E" | wt % with "F" | wt % with "G" |
|---|---|---|---|---|---|---|---|---|---|
| Phase A |  |  |  |  |  |  |  |  |  |
| Dracorin CE 614035 | Glyceryl Stearate Citrate | Symrise | 4.0 | 4.0 | 4.0 | 4.0 | 4.0 | 4.0 | 4.0 |
| Dracorin GMS 647834 | Glyceryl Stearate SE | Symrise | 1.5 | 1.5 | 1.5 | 1.5 | 1.5 | 1.5 | 1.5 |
| Lanette E | Stearyl alcohol | BASF | 1.5 | 1.5 | 1.5 | 1.5 | 1.5 | 1.5 | 1.5 |
| PCL Solid 660086 | Stearyl Heptanoate, Stearyl Caprylate | Symrise | 3.0 | 3.0 | 3.0 | 3.0 | 3.0 | 3.0 | 3.0 |
| Paraffin oil ° E | Paraffinum Liquidum | Parafluid | 6.0 | 6.0 | 6.0 | 6.0 | 6.0 | 6.0 | 6.0 |
| Dow Corning 345 | Cyclopentasiloxane, Cyclohexasiloxane | Dow Corning | 2.0 | 2.0 | 2.0 | 2.0 | 2.0 | 2.0 | 2.0 |
| Phase B |  |  |  |  |  |  |  |  |  |
| Water, demineralized | Water (Aqua) |  | Ad 100 | Ad 100 | Ad 100 | Ad 100 | Ad 100 | Ad 100 | Ad 100 |
| Carbopol ETD 2050 Polymer | Carbomer | Noveon | 0.15 | 0.15 | 0.15 | 0.15 | 0.15 | 0.15 | 0.15 |
| 1,2-Hexanediol | 1,2-Hexanediol | Symrise | — | — | 1.0 | 0.2 | — | 0.45 | 0.1 |
| 1,2-Decanediol | Decylene Glycol | Symrise | — | 1.0 | — | — | 0.25 | 0.55 | 0.2 |
| 2-Phenoxyethanol | Phenoxyethanol | Symrise | 1.0 | — | — | 0.8 | 0.75 | — | 0.7 |
| Phase C |  |  |  |  |  |  |  |  |  |
| Neutralizer AMP-95 | Amino Methylpropanol | Dow/Angus | 0.1 | 0.1 | 0.1 | 0.1 | 0.1 | 0.1 | 0.1 |
| Total: |  |  | 100.0 | 100.0 | 100.0 | 100.0 | 100.0 | 100.0 | 100.0 | pH: 5.5

The results of the preservative stress tests for *Aspergillus niger* for the combinations of active substances investigated, consisting of the mixture according to the invention (product G) or the comparative systems (products A and F), are compared in Table 2. The synergistic effect of the mixture according to the invention (product G) can be seen in the residual microbial counts after just 48 hours for *Aspergillus niger*. As can be seen from the table, in the case of *Aspergillus niger*, a particularly problematic microbe with respect to the preservation of industrial products, the microbial count was reduced within 48 hours through the use of the mixture according to the invention at a dosage of 1 wt % from 1 200 000 to 14 000. In contrast, the comparative products A to F that were tested for comparison at a dosage of 1 wt % did not, in the case of *Aspergillus niger*, allow such a significant reduction in the number of colony-forming units (CFU). This test series therefore shows, for example, that ternary mixtures of active substances according to the invention have an action that is improved synergistically relative to products A to G.

Excellent results were also obtained for the other test organisms, confirming the superiority of product G according to the invention.

Calculation of the Synergistic Antimicrobial Action of Ternary Mixtures Containing 2-Phenoxyethanol, 1,2-Decanediol and 1,2-Hexanediol To determine the potentially synergistically intensified efficacy of ternary mixtures containing 2-phenoxyethanol, 1,2-decanediol and 1,2-hexanediol, the CFU-reducing properties were determined according to the test procedure described in example 1 for the individual substances, for various binary mixtures and for ternary mixtures according to the invention. The results of the tests are presented in Table 2.

Table 2:

Test for *Aspergillus niger* CFU-reduction for 2-phenoxyethanol (product A, not according to the invention), 1,2-decanediol (product B, not according to the invention), 1,2-hexanediol (product C, not according to the invention), a binary mixture of 2-phenoxyethanol and 1,2-hexanediol (product D, not according to the invention), a binary mixture of 2-phenoxyethanol and 1,2-decanediol (product E, not according to the invention), a binary mixture of 2-phenoxyethanol and 1,2-hexanediol (product F, not according to the invention) and a ternary mixture of 2-phenoxyethanol, 1,2-decanediol and 1,2-hexanediol (product G, according to the invention) and calculated synergy index values for selected binary and ternary mixtures

|  | Total concentration used [wt %] | *Aspergillus niger* initial CFU | *Aspergillus niger* CFU after 48 h | Synergy index SI |
|---|---|---|---|---|
| 1 wt % of 2-phenoxyethanol (product A) | 1 | 1200000 | 1100000 | ./. |
| 1 wt % of 1,2-decanediol (product B) | 1 | 1200000 | 1200000 | ./. |
| 1 wt % of 1,2-hexanediol (product C) | 1 | 1200000 | 1000000 | ./. |
| 0.70 wt % of 2-phenoxyethanol and 0.20 wt % of 1,2-decanediol and 0.10 wt % of 1,2-hexanediol (product G) | 1 | 1200000 | 14000 | 0.0129 |

Result:

The synergy index (SI values) of the ternary mixtures according to the invention and binary mixtures not according to the invention according to Kull (literature: F. C. Kull et al., Applied Microbiology Vol. 9, p. 538-541 (1961); D. C. Steinberg, Cosmetics & Toiletries Vol. 115(11), 59-62 (2000) was calculated using the following equations.

Binary mixtures: $SI = Z*D/A + Z*E/B$

Ternary mixture: $SI = Z*D/A + Z*E/B + Z*F/C$ wherein:
D, E, F: factor of proportion of the individual constituents (e.g. 70 wt %=factor 0.70)
A, B, C: CFU of the individual substances at time point 48 h
Z: CFU of the binary/ternary mixture at time point 48 h A synergistic effect is present if values below 1.00 are obtained. Values above 1.00 show an antagonistic effect. At a value of exactly 1.00 there is neither a synergistic nor an antagonistic effect.

The calculation of the synergy index for the ternary mixture according to the invention containing 0.70 wt % of 2-phenoxyethanol, 0.20% of 1,2-decanediol and 0.10 wt % of 1,2-hexanediol is shown below.

$SI = 14\ 000*0.70/1\ 100\ 000 + 14\ 000*0.20/1\ 200\ 000 + 14\ 000*0.10/1\ 000\ 000 = 0.0126$

The SI value of 0.0126 shows a highly significant, synergistically intensified action of the mixture containing 2-phenoxyethanol, 1,2-decanediol and 1,2-hexanediol.

The results presented in Table 2 and in particular those for the calculated synergy indices clearly show that the ternary mixture according to the invention (product G) containing 2-phenoxyethanol, 1,2-decanediol and 1,2-hexanediol has a definitely synergistically intensified antimicrobial action. In the case of the binary mixtures (products D-F) no significant synergy effect was detected, on the contrary, in some cases even a negative synergy effect (intensified microbial growth) was observed compared with the use of mixtures A, B and C.

It can be concluded from this that the surprisingly clear synergy effect in the ternary mixture once again, surprisingly, is not due to an effect of mixing just two components of the 3-component system.

A synergistic effect as shown in example 1 was achieved in another example, for a ternary mixture containing 2-phenoxyethanol, 1,2-decanediol and 1,2-pentanediol as a substitute for 1,2-hexanediol. The synergistic intensification of the action of these ternary mixtures can be attributed to better availability of phenoxyethanol and 1,2-decanediol in the aqueous phase on adding 1,2-hexanediol or 1,2-pentanediol. Short-chain antimicrobially effective diols such as 1,2-hexanediol or 1,2-pentanediol can serve as solubilisers, which increase the concentration of the far more strongly antimicrobially effective substances 2-phenoxyethanol and 1,2-decanediol in the aqueous phase of emulsions, the living space of the microorganisms.

Example 2

Cosmetic/Dermatological Practical Examples

For application, the dermatological and cosmetic preparations containing synergistically effective ternary mixtures are applied in sufficient amount in combination with other cosmetic active substances and additives on the skin and/or on the hair in the usual way for cosmetics. Examples of advantageous preparations for some uses are given below:

Creams for Regulating Skin Moisture:

| Phase | Ingredient | INCI | wt % | wt % |
|---|---|---|---|---|
| A | Dracorin CE | Glyceryl stearate citrate | 4.00 | |
| A | Cutina GMS | Glyceryl stearate | 1.50 | 1.50 |
| A | Lanette 18 | Stearyl alcohol | 1.50 | 3.00 |
| A | PCL Solid | Stearyl heptanoate, stearyl caprylate | 3.00 | 2.00 |
| A | Emulsiphos | Potassium Cetyl Phosphate, Hydrogenated Palm Glycerides | | 1.50 |
| A | Mineral Oil | Mineral oil | 6.00 | 4.00 |
| A | Dow Corning 345 | Cyclopentasiloxane, Cyclohexasiloxane | 2.00 | 2.00 |
| A | Dragoxat 89 | Ethylhexyl Isononanoate | | 4.00 |
| B | Water | Water | 77.15 | 78.60 |
| B | Carbopol ETD 2050 | Carbomer | 0.25 | |
| B | Disodium EDTA | Disodium EDTA | 0.10 | 0.10 |
| B | Xanthan gum | | | 0.30 |
| C | NAOH 10% solution | NAOH 10% solution | 0.50 | |
| C | Zemea | 1,3-Propanediol | 2.00 | |
| C | Hydrolite 5 | Pentylene glycol | | 2.00 |
| C | SYMGlucan | Water, Glycerin, Beta-Glucan | 1.00 | |
| D | 2-Phenoxyethanol, 1,2-decanediol, 1,2-hexanediol (7:2:1) | Phenoxyethanol, Decylene Glycol, 1,2-Hexanediol | 1.00 | 0.60 |
| D | Fragrance | Fragrance | | 0.40 |

Sunscreen Formulation:

| Phase | Ingredient | INCI | wt % | wt % |
|---|---|---|---|---|
| A | Dracorin CE | Glyceryl stearate citrate | | |
| A | Neo Heliopan BB | Benzophenone-3 | 6.00 | 1.50 |
| A | Lanette 18 | Stearyl alcohol | 1.50 | 1.00 |
| A | Neo Heliopan HMS | Homosalate | 10.00 | |
| A | Neo Heliopan OS | Ethylhexyl Salicylate | 5.00 | |
| A | Neo Heliopan 357 | Avobenzone | 3.00 | 1.50 |
| A | Neo Heliopan AV | Ethylhexyl Methoxycinnamate | 7.50 | |
| A | Neo Heliopan 303 | Octocrylene | | 10.00 |
| A | Tocopheryl Acetate | Tocopheryl Acetate | | 0.20 |
| A | Ethylhexyl Triazone | Ethylhexyl Triazone | | 1.00 |
| A | PCL Solid | Stearyl heptanoate, stearyl caprylate | 2.00 | |
| A | Emulsiphos | Potassium Cetyl Phosphate, Hydrogenated Palm Glycerides | 2.00 | |
| A | Tegosoft TN | C12-15 Alkyl Benzoate | 3.00 | |
| A | Neutral Oil | Caprylic/capric triglyceride | 3.00 | |
| A | Dragoxat 89 | Ethylhexyl Isononanoate | 2.00 | |
| A | Xanthan gum | | 0.20 | |
| A | Tegosoft XC | Phenoxyethyl caprylate | | 5.00 |
| A | Tegosoft DC | Decyl Cocoate | | 2.50 |
| B | Butylene glycol | Butylene glycol | | 2.00 |
| B | Tego Care CG 90 | Cetearyl Glucoside | | 1.00 |
| B | Water | Water | 51.10 | 72.35 |
| B | Carbopol ETD 2050 | Carbomer | 0.20 | 0.05 |
| B | Disodium EDTA | Disodium EDTA | 0.10 | 0.10 |
| B | Tego Carbomer 341 ER | Acrylates/C10-30 Alkyl Acrylate Crosspolymer | | 0.05 |
| C | AMP Ultra | Aminomethyl Propanol | 0.15 | 0.10 |
| C | Glycerin | Glycerin | 2.00 | |
| D | 2-Phenoxyethanol, 1,2-decanediol, 1,2-hexanediol (7:2:1) | Phenoxyethanol, Decylene Glycol, 1,2-Hexanediol | 1.00 | 1.25 |
| D | Perfume Oil | Fragrance | 0.25 | 0.40 |

Shampoo Formulation:

| Phase | Ingredient | INCI | wt % | wt % |
|---|---|---|---|---|
| A | Water | Water | 50.70 | 57.90 |
| A | Aculy 88 | Acrylate/Steareth-20 Methacrylate Crosspolymer | | 3.45 |
| A | Novethix L-10 | Acrylate/Beheneth-25 Methacrylate Copolymer | 2.50 | |
| B | Plantapon SF | Sodium Cocoamphoacetate, Glycerol, Lauryl Glucoside, Sodium Cocoyl Glutamate, Sodium Lauryl Glucose Carboxylate | 30.00 | |
| B | Plantacare 2000 UP | Decyl Glucoside E | 3.00 | |
| B | Lamesoft PO 65 | Coco-Glucoside, Glyceryl Oleate | 5.00 | |
| B | Stepanol AMV | Ammonium Lauryl Sulphate | | 10.00 |
| B | Sodium Laureth Sulphate 28% | Sodium Laureth Sulphate | | 10.00 |
| C | Dehyton AB 30 | Coco Betaine | 7.00 | |
| C | Triethanolamine | Triethanolamine | | 1.50 |
| C | Mackanate EL 40% | Disodium Laureth Sulphosuccinate | | 8.00 |
| C | Cocamidopropyl Betaine 30% | Cocamidopropyl Betaine | | 4.00 |
| C | PEG-12 Dimethicone | PEG-12 Dimethicone | | 2.00 |
| C | Disodium EDTA | Disodium EDTA | 0.10 | 0.10 |
| C | Polyquaternium-10 | Polyquaternium-10 | | 0.25 |
| C | NAOH 10% solution | NAOH 10% solution | 0.20 | |
| C | Propylene Glycol | Propylene Glycol | | 2.00 |
| D | 2-Phenoxyethanol, 1,2-decanediol, 1,2-hexanediol (7:2:1) | Phenoxyethanol, Decylene Glycol, 1,2-Hexanediol | 1.00 | 0.80 |
| D | Perfume Oil | Fragrance | 0.50 | |

Formulations for Decorative Cosmetics:

| Phase | Ingredient | INCI | wt % | wt % |
|---|---|---|---|---|
| A | Abil Wax 2440 | Behenoxy Dimethicone | 2.00 | |
| A | Isodragol | Triisononanoin | | 2.00 |
| A | Cetearyl Ethylhexanoate | Cetearyl Ethylhexanoate | 5.50 | |
| A | Rewopal PIB 1000 | Polyisobutene | 5.00 | |
| A | Dragoxat 89 | Ethylhexyl Isononanoate | 8.00 | |
| A | Talc | Talc | | 4.00 |
| A | PVP/Eicosene Copolymer | PVP/Eicosene Copolymer | 0.25 | |
| A | Polydecene | Polydecene | | 3.00 |
| A | Titanium Dioxide | Titanium Dioxide | | 6.00 |
| A | Iron Oxides | Iron Oxides | | 1.60 |
| B | Myristyl Lactate | Myristyl Lactate | 8.00 | |
| B | Candelilla Wax | Candelilla Wax | 7.50 | |
| B | Copernicia Cerifera (Carnauba) Wax | Copernicia Cerifera (Carnauba) Wax | 2.50 | |
| B | Dimethyl Isosorbide | Dimethyl Isosorbide | 3.00 | |
| B | Covapate Unired LC3728 | Ricinus Communis (Castor) Seed Oil, Cl 45410 | 3.90 | |
| B | Ceresin | Ceresin | 3.00 | |
| B | Covapate Uniwhite LC7981 | Ricinus Communis (Castor) Seed Oil, Cl 77891 | 9.60 | |
| B | Rubis Covapate W4765 | Ricinus Communis (Castor) Seed Oil, Cl 15850; | 1.45 | |
| B | Brun Covapate W8760 | Ricinus Communis (Castor) Seed Oil, Iron Oxides | 5.50 | |
| B | Lanolin Oil | Lanolin Oil | 18.00 | |
| B | Lanolin | Lanolin | 16.00 | |
| B | Tocopheryl Acetate | Tocopheryl Acetate | 0.20 | |
| B | Cyclopentasiloxane, Cyclohexasiloxane | Cyclopentasiloxane, Cyclohexasiloxane | | 18.00 |
| B | Abil EM 97 | Bis-PEG/PPG-14/14 Dimethicone | | 2.80 |
| B | Phenyl Trimethicone | Phenyl Trimethicone | | 1.00 |
| C | Water | Water | | 53.55 |
| C | Sodium Chloride | Sodium Chloride | | 1.25 |
| C | Propylene Glycol | Propylene Glycol | | 6.00 |
| C | 2-Phenoxyethanol, 1,2-Decanediol, 1,2-Hexanediol (7:2:1) | Phenoxyethanol, Decylene Glycol, 1,2-Hexanediol | 0.50 | 0.80 |
| C | Perfume Oil | Fragrance | 0.10 | |

Example 3

Further Formulations Containing Ternary Antimicrobial Mixtures According to the Invention In the following table:

| NAME OF RAW MATERIAL (MANUFACTURER) | INCI | 3.1 | 3.2 | 3.3 | 3.4 | 3.5 | 3.6 | 3.7 | 3.8 | 3.9 | 3.10 |
|---|---|---|---|---|---|---|---|---|---|---|---|
| 2-Phenoxyethanol | Phenoxyethanol | 0.7 | 0.7 | 1.0 | 0.7 | 1.4 | 0.7 | 0.7 | 1.05 | 0.7 | 0.7 |
| SymClariol (Symrise) | Decylene Glycol | 0.2 | 0.2 | 0.4 | 0.2 | 0.4 | 0.2 | 0.2 | 0.3 | 0.2 | 0.2 |
| Hydrolite-6 (Symrise) | 1,2-Hexanediol | 0.1 | | 0.2 | 0.1 | | | 0.1 | | 0.1 | |
| Hydrolite-5 (Symrise) | Pentylene Glycol | | 0.1 | | | 0.2 | 0.1 | | 0.15 | | 0.1 |
| -(-Alpha-)-Bisabolol, natural (Symrise) | Bisabolol | 0.3 | 0.4 | 0.3 | 0.1 | 0.3 | 0.2 | 0.05 | 0.2 | 0.5 | 0.1 |
| Ginger $CO_2$ Extract (Flavex) | Zingiber Officinale (Ginger) Root Extract | 0.003 | 0.004 | 0.003 | 0.005 | 0.003 | 0.002 | 0.001 | 0.002 | 0.01 | 0.001 |
| Abil 350 (Degussa-Goldschmidt) | Dimethicone | 0.5 | 2.0 | 1.0 | | | | | 0.5 | 0.5 | |
| Allantoin (Merck) | Allantoin | | | 0.2 | 0.1 | | | | | | |
| Aloe Vera Gel Concentrate 10/1 (Symrise) | Water (Aqua), Aloe Barbadensis Leaf Juice | | | | 3.0 | | 3.0 | | | | |

-continued

| NAME OF RAW MATERIAL (MANUFACTURER) | INCI | WT % | | | | | | | | | |
|---|---|---|---|---|---|---|---|---|---|---|---|
| | | 3.1 | 3.2 | 3.3 | 3.4 | 3.5 | 3.6 | 3.7 | 3.8 | 3.9 | 3.10 |
| Alugel 34 TH (Baerlocher) | Aluminium Stearate | | | | | | 1.0 | | | | |
| Aqua-Ceramide (Kao) | Cetyloxypropyl Glyceryl Methoxypropyl Myristamide | | 0.1 | | | | | | | | 0.1 |
| Arbutin (Sabinsa) | β-Arbutin | 1.0 | | | | | | | | | |
| Sodium Ascorbyl Phosphate (EMD Chemicals) | Sodium Ascorbyl Phosphate | 2.0 | | 1.0 | | | | | | | |
| Butylene Glycol | Butylene Glycol | | | 5.0 | | | | | | | |
| Carbopol ETD 2050 (Noveon) | Carbomer | | | | | 0.2 | | | | | |
| Carbopol Ultrez-10 (Noveon) | Carbomer | | 0.1 | | | | | | | | |
| Ceramide 2 (Sederma) | Ceramide 2 | 0.1 | | | | | | | | | |
| Ceramide PC104 (Pacific Corporation) | Hydroxypropyl Bispalmitamide MEA | | | | | 0.1 | | | | | |
| Ceramide SL (Sino Lion) | Hydroxyethyl Palmityl Oxyhydroxypropyl Palmitamide | | | | | | | 0.1 | | | |
| Cetiol OE (Cognis) | Dicaprylyl Ether | | | | 4.0 | | | | | | |
| Cetiol SB 45 (Cognis) | Butyrospermum Parkii (Shea Butter) | | | | 1.0 | | | | | | |
| Citric Acid 10% sol. | Citric Acid | | | | | | | | 0.3 | | |
| Comperlan 100 (Cognis) | Cocamide MEA | | | | | | | | 0.5 | | |
| Dihydroxyacetone (Merck) | Dihydroxyacetone | | | | | | | | | 5.0 | |
| Dow Corning 246 Fluid (Dow Corning) | Cyclohexasiloxane and Cyclopentasiloxane | | | | | | 2.0 | | | | |
| Dow Corning 345 Fluid (Dow Corning) | Cyclomethicone | | | | | 0.5 | | | | | |
| D-Panthenol (BASF) | Panthenol | | | | 1.0 | | | | | | |
| Dracorin CE (Symrise) | Glyceryl Stearate Citrate | 5.0 | | | | | | | 5.0 | | 1.5 |
| Dracorin GMS (Symrise) | Glyceryl Stearate | | 2.0 | | | | | | | 2.0 | |
| Dracorin GOC (Symrise) | Glyceryl Oleate Citrate, Caprylic/Capric Triglyceride | | | | 2.0 | | | | | | |
| Drago-Beta-Glucan (Symrise) | Water (Aqua), Butylene Glycol, Glycerin, Avena Sativa (Oat), Kernel Extract | 0.3 | | | | | | | | | |
| Dragocid Liquid (Symrise) | Phenoxyethanol, Methylparaben, Ethylparaben, Butylparaben, Propylparaben, Isobutylparaben | | 0.8 | 0.7 | | 0.7 | 0.8 | | | 0.8 | |
| Dragoderm (Symrise) | Glycerin, Triticum Vulgare (Wheat) Gluten, Water (Aqua) | | | | | | | | 2.0 | | |
| Drago-Oat-Active (Symrise) | Water (Aqua), Butylene Glycol, Avena Sativa (Oat) Kernel Extract | | | | 1.0 | | | | | | |
| Dragosan W/O Liquid (Symrise) | Polyglyceryl-3-Polyricinoleate, Sorbitan Isostearate | | | | | | | 1.0 | | | |

-continued

| NAME OF RAW MATERIAL (MANUFACTURER) | INCI | WT % | | | | | | | | | |
|---|---|---|---|---|---|---|---|---|---|---|---|
| | | 3.1 | 3.2 | 3.3 | 3.4 | 3.5 | 3.6 | 3.7 | 3.8 | 3.9 | 3.10 |
| Dragosan W/O P (Symrise) | Sorbitan Isostearate, Hydrogenated Castor Oil, Ceresin, Beeswax (Cera Alba) | | | | | | 6.0 | | | | |
| Dragoxat EH (Symrise) | Ethylhexyl Ethylhexanoate | 3.0 | 3.0 | | 4.0 | | | | 3.0 | | |
| Dragoxat 89 (Symrise) | Ethylhexyl Ethylisononanoate | | | | | | | | | 2.0 | |
| EDETA B Powder (BASF) | Tetrasodium EDTA | | | | | | | 0.1 | | | |
| EDETA DB (BASF) | Disodium EDTA | | | | | 0.1 | | | 0.1 | | |
| Emulsiphos (Symrise) | Potassium Cetyl Phosphate, Hydrogenated Palm Glycerides | | 2.0 | | | 1.5 | | | | 2.0 | |
| Ethanol 96% | Ethanol | | | | | | | | 2.0 | | 30.0 |
| Extrapone Green Tea GW (Symrise) | Glycerin, Water (Aqua), Camellia Sinensis Leaf Extract | | 0.2 | | | | | | | | |
| Extrapone Witch Hazel Distillate colorless (Symrise) | Propylene Glycol, Hamamelis Virginiana (Witch Hazel) Water, Water (Aqua), Hamamelis Virginiana (Witch Hazel) Extract | | | | | | | 1.0 | | | |
| Extrapone Rosemary GW (Symrise) | Glycerin, Water (Aqua), Rosmarinus officinalis (Rosemary) Leaf Extract | | | 0.3 | | | | | | 0.5 | |
| Farnesol (Symrise) | Farnesol | | | | | | | | | | 0.5 |
| Frescolat ML cryst. (Symrise) | Menthyl Lactate | | | | 0.8 | | | | | | |
| Genapol LRO liquid (Cognis) | Sodium Laureth Sulfate | | | | | | | 37.0 | | | |
| Givobio GZN (Seppic) | Zinc Gluconate | | | | | | | | | 0.5 | |
| Glycerin 85% | Glycerin | 3.0 | 2.0 | 4.0 | | 4.7 | 2.0 | | 1.5 | 3.0 | |
| Hydroviton (Symrise) | Water, Glycerin, Sodium Lactate, TEA Lactate, Serine, Lactic Acid, Urea, Sorbitol, Sodium Chloride, Lauryl Diethylene-diaminoglycine, Lauryl Aminopropylglycine, Allantoin | | | | | | | | | 1.0 | |
| Irgasan DP 300 (Ciba Geigy) | Triclosan | | | | | | | | | | 0.3 |
| Isodragol (Symrise) | Triisononanoin | | 2.0 | | | | | | | 3.0 | |
| Isopropylpalmitate (Symrise) | Isopropyl Palmitate | 4.0 | | | | | | | 4.0 | | |
| Karion F (Merck) | Sorbitol | | | | | | 2.0 | | | | |
| Keltrol RD (CP-Kelco) | Xanthan Gum | 0.2 | 0.1 | | | | | | | | |
| Keltrol T (Danby-Chemie) | Xanthan Gum | | | | | 0.2 | | | 0.3 | | |
| Kojic acid (Cosmetochem) | Kojic acid | 1.0 | | | | | | | | | |
| Lanette 16 (Cognis) | Cetyl Alcohol | 1.0 | | | | | | | 1.0 | | |
| Lanette O (Cognis) | Cetearyl Alcohol | | 3.0 | | | 1.0 | | | | 2.0 | |
| Lara Care A-200 (Rahn) | Galactoarabinan | | | 0.3 | | | | | | | |
| Magnesium Chloride (Merck) | Magnesium Chloride | | | | | | | 0.7 | | | |

-continued

| NAME OF RAW MATERIAL (MANUFACTURER) | INCI | WT % | | | | | | | | | |
|---|---|---|---|---|---|---|---|---|---|---|---|
| | | 3.1 | 3.2 | 3.3 | 3.4 | 3.5 | 3.6 | 3.7 | 3.8 | 3.9 | 3.10 |
| Merquat 550 (Ondeo Nalco) | Polyquaternium-7 | | | | | | | 0.5 | | | |
| NADH 10% sol. | Sodium Hydroxide | | | | | | | | | 0.3 | |
| Naringin (Exquim) | 4',5,7-Trihydroxyflavone-7-O-neohesperidoside | | | | | | | 0.5 | 2.0 | | |
| Sodium benzoate | Sodium Benzoate | | | | | | | 0.5 | | | |
| Natrosol 250 HHR (Aqualon) | Hydroxyethyl cellulose | | | | | | | | | | 0.3 |
| Neo Heliopan 357 (Symrise) | Butyl Methoxy-dibenzoylmethane | | | | | 1.0 | | | | | |
| Neo Heliopan AP (Symrise) (10% as sodium salt) | Disodium Phenyl Dibenzimidazole Tetrasulfonate | | | | | 10 | | | | | |
| Neo Heliopan AV (Symrise) | Ethylhexyl Methoxycinnamate | | | | | 3.0 | | | | | |
| Neo Heliopan Hydro (Symrise) (15% as sodium salt) | Phenylbenzimidazole Sulfonic Acid | | | | | 6.7 | | | | | |
| Neo Heliopan MBC (Symrise) | 4-Methylbenzylidene Camphor | | | | | 1.5 | | | | | |
| Neo Heliopan OS (Symrise) | Ethylhexyl Salicylate | | | | | 5.0 | | | | | |
| Neutral Oil | Caprylic/Capric Triglyceride | 6.0 | | | 4.0 | 2.0 | | | 6.0 | 10.0 | |
| Oxynex 2004 (Merck) | BHT | | | | | | 0.1 | | | | |
| Paraffin oil 5 Grade E (Parafluid) | Paraffinum Liquidum | | | | 4.0 | | | | | | |
| PCL Liquid 100 (Symrise) | Cetearyl Ethylhexoate | 3.0 | 5.0 | | 7.0 | | | | | | |
| PCL Solid (Symrise) | Stearyl Heptanoate, Stearyl Caprylate | | 2.0 | | | | | | | | |
| PCL-Liquid (Symrise) | Cetearyl Ethylhexanoate, Isopropyl Myristate | | | | | | | 12.0 | 3.0 | | |
| Pemulen TR-2 (Noveon) | Acrylates/C10-30 Alkyl Acrylate Crosspolymer | | | 0.3 | 0.2 | | | | | | |
| 4-(1-Phenylethyl)1,3-benzenediol | 4-(1-Phenylethyl)1,3-benzenediol | 0.5 | | | | | | | | | |
| Propylene Glycol-1,2 99P GC | Propylene Glycol | | 5.0 | | | | | | | | |
| Pseudoceramide 391 | N-(1-Hexadecanoyl)-4-hydroxy-L-proline-(1-hexadecyl-ester | | 0.1 | | | | | 0.2 | | 0.5 | |
| Retinyl Palmitate in Oil (DSM Nutrional Products) | Retinyl Palmitate | | | | | | 0.2 | | | | |
| Sepigel 305 | Polyacrylamide, C13-14 Isoparaffin, Laureth-7 | | | | | | | | 1.0 | | |
| Sodium Chloride | Sodium Chloride | | | | | | | | 1.0 | | |
| Sodium Hydroxide (10% sol. | Sodium Hydroxide | | 0.3 | 0.6 | 0.4 | | | | | | |
| Solubilizer 611674 (Symrise) | PEG-40 Hydrogenated Castor Oil, Trideceth-9, Water (Aqua) | | | | | | | | | | 2.0 |
| Sun Flower Oil (Wagner) | *Helianthus Annuus* (Sunflower) Seed Oil | | | | | | 5.0 | | | | |
| Sweet Almond Oil (Wagner) | *Prunus dulcis* | | | | | | 5.0 | | | | |
| Symdiol 68 (Symrise) | 1,2 Hexanediol, Caprylylglycol | 0.5 | | | | | | | | | |
| Symrise Fragrance | Fragrance | 0.3 | 0.3 | 0.3 | 0.2 | 0.4 | 0.4 | 0.5 | 0.3 | 0.3 | 1.0 |
| Tamasterol (Tama Biochemicals) | Phytosterols | | | | | | | | | 0.3 | |

-continued

| NAME OF RAW MATERIAL (MANUFACTURER) | INCI | WT % | | | | | | | | | |
|---|---|---|---|---|---|---|---|---|---|---|---|
| | | 3.1 | 3.2 | 3.3 | 3.4 | 3.5 | 3.6 | 3.7 | 3.8 | 3.9 | 3.10 |
| Tego Betaine L7 (Degussa) | Cocamidopropyl Betaine | | | | | | | 6.0 | | | |
| Tegosoft PC 31 (Degussa) | | | | | | | | | | 0.3 | |
| Tegosoft TN (Degussa) | C12-15 Alkyl Benzoate | | | 5.0 | | 5.0 | | | | | |
| Triethanolamine, 99% | Triethanolamine | | | | | 0.5 | | | | | |
| Tocopherol Acetate (DSM Nutritional Products) | Tocopheryl Acetate | | | 0.5 | 0.5 | | 3.0 | | | 0.3 | |
| Zirkonal L 450 (BK Giulini) | Aluminium Zirconium Pentachlorohydrate (40% aqueous solution) | | | | | | | | | | 37.0 |
| Water, demineralised | Water (Aqua) | ad 100 | ad 100 | ad 100 | ad 100 | ad 100 | ad 100 | ad 100 | ad 100 | ad 100 | ad 100 |

3.1 = skin-lightening day cream O/W
3.2 = skin calming lotion with plant extracts O/W
3.3 = after sun balm
3.4 = body spray
3.5 = sunscreen lotion (O/W), broadband protection
3.6 = W/O night cream
3.7 = shampoo
3.8 = self-tanning cream
3.9 = barrier repair cream O/W
3.10 = antiperspirant/deodorant roll-on

The invention claimed is:

1. A cosmetic or pharmaceutical preparation or foodstuff comprising an antimicrobially effective mixture, wherein the antimicrobially effective mixture consists of:
   (a) 2-phenoxyethanol,
   (b1) 1,2-decanediol, and
   (b2) 1,2-hexanediol and/or 1,2-pentanediol and/or 1,2-octanediol.

2. The cosmetic or pharmaceutical preparation or foodstuff according to claim 1, wherein the antimicrobially effective mixture consists of:
   (a) 2-phenoxyethanol,
   (b1) 1,2-decanediol, and
   (b2) 1,2-hexanediol and/or 1,2-pentanediol.

3. The cosmetic or pharmaceutical preparation or foodstuff according to claim 1, wherein the total amount of the antimicrobially effective mixture is in the range from 0.01 to 10 wt %, relative to the total mass of the preparation or of the foodstuff.

4. The cosmetic or pharmaceutical preparation or foodstuff according to claim 2 comprising:
   0.30 to 1.20 wt % of 2-phenoxyethanol,
   0.05 to 0.40 wt % of 1,2-decanediol, and
   0.01 to 0.30 wt % of the total amount of 1,2-hexanediol and/or 1,2-pentanediol, in each case relative to the total mass of the preparation or of the foodstuff.

* * * * *